(12) United States Patent
Roke et al.

(10) Patent No.: US 9,778,177 B2
(45) Date of Patent: Oct. 3, 2017

(54) DEVICE AND METHOD FOR MEASURING AND IMAGING SECOND HARMONIC AND MULTI-PHOTON GENERATION SCATTERED RADIATION

(71) Applicant: ÉCOLE POLYTECHNIQUE FÉDÉRALE DE LAUSANNE (EPFL), Lausanne (CH)

(72) Inventors: Sylvie Roke, Lausanne (CH); Carlos Macias Romero, Lausanne (CH)

(73) Assignee: ÉCOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 313 days.

(21) Appl. No.: 14/599,871

(22) Filed: Jan. 19, 2015

(65) Prior Publication Data

US 2015/0233820 A1    Aug. 20, 2015

Related U.S. Application Data

(63) Continuation-in-part of application No. PCT/EP2013/064723, filed on Jul. 11, 2013.

(30) Foreign Application Priority Data

Jul. 17, 2012 (EP) .................................. 12176708

(51) Int. Cl.
*G01N 21/00* (2006.01)
*G01N 21/47* (2006.01)
(Continued)

(52) U.S. Cl.
CPC .......... *G01N 21/47* (2013.01); *G01N 15/1434* (2013.01); *G01N 21/21* (2013.01);
(Continued)

(58) Field of Classification Search
CPC .... G01N 15/1434; G01N 21/21; G01N 21/47; G01N 2201/06113; G01N 2201/0683;
(Continued)

(56) References Cited

U.S. PATENT DOCUMENTS 6,055,051 A    4/2000 Eisenthal
2010/0031748 A1   2/2010 Simpson et al.

FOREIGN PATENT DOCUMENTS

EP    0 740 156    10/1996
WO   WO-02/46764    6/2002

OTHER PUBLICATIONS

Campagnola, P.J., et al., "High-Resolution Nonlinear Optical Imaging of Live Cells by Second Harmonic Generation," *Biophysical Journal*, Dec. 1999, vol. 77, pp. 3341-3349.
(Continued)

*Primary Examiner* — Tri T Ton
(74) *Attorney, Agent, or Firm* — Saliwanchik, Lloyd & Eisenschenk

(57) ABSTRACT

Embodiments of the subject invention relate to a method and apparatus for performing measurements using multiphoton or second harmonic generation (SHG) scattered radiation from a sample including a turbid (scattering) medium includes providing a beam of laser pulses from a laser source having high pulse energies and a repetition rate; splitting the beam of laser pulses into two or more partial beams and focussing and overlaying the partial beams on a sample including the turbid medium; and detecting multiphoton and second harmonic radiation scattered from the sample.

21 Claims, 7 Drawing Sheets

(51) Int. Cl.
G02F 1/37 (2006.01)
G01N 15/14 (2006.01)
G01N 21/21 (2006.01)
G02B 21/36 (2006.01)

(52) U.S. Cl.
CPC ............ *G02B 21/361* (2013.01); *G02F 1/37* (2013.01); *G01N 2201/0683* (2013.01); *G01N 2201/0697* (2013.01); *G01N 2201/06113* (2013.01)

(58) Field of Classification Search
CPC ........... G01N 2201/0697; G01N 21/49; G01N 21/636; G02B 21/361; G02F 1/37
See application file for complete search history.

(56) References Cited

OTHER PUBLICATIONS

Cho, S.H., et al., "Generation of 90-nJ pulses with a 4-MHz repetition-rate Kerr-lens mode-locked Ti:Al$_2$O$_3$ laser operating with net positive and negative intracavity dispersion," *Optics Letters*, Apr. 15, 2001, vol. 26, No. 8, pp. 560-562.

Dadap, J.I., et al., "Nonlinear light scattering from clusters and single particles," *The Journal of Chemical Physics*, 2009, vol. 130, pp. 214710-1-214710-7.

Del Barco, O., et al., "Second harmonic generation signal in collagen fibers: role of polarization, numerical aperture, and wavelength," *Journal of Biomedical Optics*, Apr. 2012, vol. 17, No. 4, pp. 045005-1-045005-8.

Dombeck, D.A., et al., "Uniform polarity microtubule assemblies imaged in native brain tissue by second-harmonic generation microscopy," *Proceedings of the National Academy of Sciences*, Jun. 10, 2003, vol. 100, No. 12, pp. 7081-7086.

Freund, I., et al., "Optical Second-harmonic Microscopy, Crossed-beam Summation, and Small-angle Scattering in Rat-tail Tendon," *Biophysical Journal*, Oct. 1986, vol. 50, pp. 693-712.

Haber, L.H., et al., "Probing the colloidal gold nanoparticle/aqueous interface with second harmonic generation," *Chemical Physics Letters*, 2011, vol. 507, pp. 11-14.

Jen, S.H., et al., "The Effect of Particle Size in Second Harmonic Generation from the Surface of Spherical Colloidal Particles. I: Experimental Observations," *The Journal of Physical Chemistry A*, 2009, vol. 113, pp. 4758-4762.

Kriech, M.A., et al., "Imaging Chirality with Surface Second Harmonic Generation Microscopy," *Journal of the American Chemical Society*, 2006, vol. 127, pp. 2834-2835.

Kuetemeyer, K., et al., "Influence of laser parameters and staining on femtosecond laser-based intracellular nanosurgery," *Biomedical Optics Express*, Sep. 1, 2010, vol. 1, No. 2, pp. 587-597.

Le Harzic, R., et al., "Influence of femtosecond laser pulse irradiation on the viability of cells at 1035, 517, and 345 nm," *Journal of Applied Physics*, 2007, vol. 102, pp. 114701-1-114701-4.

Liu, Y., et al., "Surface Potential of Charged Liposomes Determined by Second Harmonic Generation," *Langmuir*, 2001, vol. 17, pp. 2063-2066.

Masters, B., et al. (ed.), *Handbook of Biomedical Nonlinear Optical Microscopy*, Oxford University Press, Oxford, 2008.

Maurer, C., et al., "What spatial light modulators can do for optical microscopy," *Laser & Photonics Reviews*, 2011, vol. 5, No. 1, pp. 81-101.

Mertz, J., "Optical sectioning microscopy with planar or structured illumination," *Nature Methods*, Oct. 2011, vol. 8, No. 10, pp. 811-819.

Nikolenko, V., et al., "SLM microscopy: scanless two-photon imaging and photostimulation with spatial light modulators," *Frontiers in Neural Circuits*, Dec. 2008, vol. 2, Article 5, pp. 1-14.

Nuriya, M., et al., "Imaging membrane potential in dendritic spines," *Proceedings of the National Academy of Sciences*, Jan. 17, 2006, vol. 103, No. 3, pp. 786-790.

Oron, D., et al., "Scanningless depth-resolved microscopy," *Optics Express*, Mar. 7, 2005, vol. 13, No. 5, pp. 1-9.

Pantazis, P. et al., "Second harmonic generating (SHG) nanoprobes for in vivo imaging," *Proceedings of the National Academy of Sciences*, Aug. 17, 2010, vol. 107, No. 33, pp. 14535-14540.

Peterson, M.D., et al., "Second harmonic generation imaging with a kHz amplifier [Invited]," *Optical Materials Express*, May 1, 2001, vol. 1, No. 1, pp. 57-66.

Roke, S., et al., "Nonlinear Light Scattering and Spectroscopy of Particles and Droplets in Liquids," *Annual Review of Physical Chemistry*, 2012, vol. 63, pp. 353-378.

Schürer, B., et al., "Probing colloidal interfaces by angle-resolved second harmonic light scattering," *Physical Review B*, 2010, vol. 82, pp. 241404-1-241404-4.

Shan, J., et al., "Experimental study of optical second-harmonic scattering from spherical nanoparticles," *Physical Review A*, 2006, vol. 73, pp. 023819-1-023819-4.

Wang, H., et al., "Second harmonic generation from the surface of centrosymmetric particles in bulk solution," *Chemical Physics Letters*, Aug. 30, 1996, vol. 259, pp. 15-20.

Yang, N., et al., "Angle-Resolved Second-Harmonic Light Scattering from Colloidal Particles," *Physical Review Letters*, Sep. 3, 2001, vol. 87, No. 10, pp. 103902-1-103902-4.

Major, A., et al., "Ultrafast Yb:KGd(WO$_4$)$_2$ laser for multimodal biomedical imaging with reduced photodamage," *Proceedings of SPIE*, Feb. 7, 2008, vol. 688108, pp. 1-7.

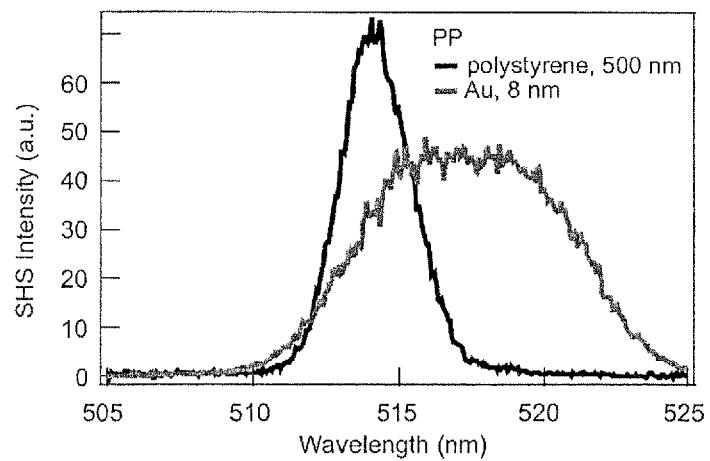
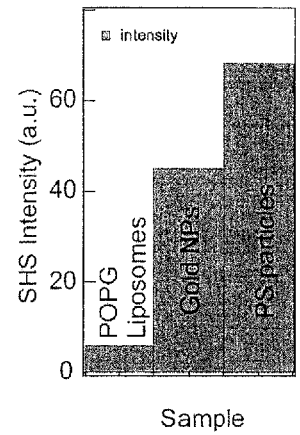
FIG. 6A
FIG. 6B
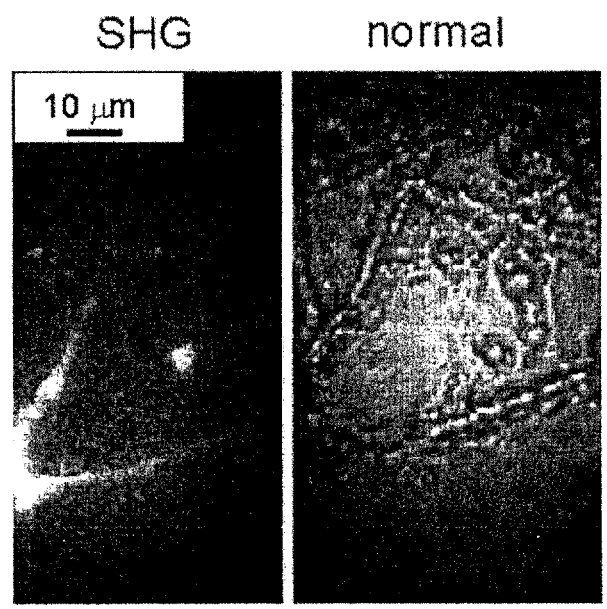
FIG. 7A
FIG. 7B

Wide-field image (Gold electrodes)    2nd harmonic image (Disconnected)    2nd harmonic image (1.5 Volts)    Line scans of different voltages Wide-field image (Neuron)    Second harmonic image (time averaged)

DEVICE AND METHOD FOR MEASURING AND IMAGING SECOND HARMONIC AND MULTI-PHOTON GENERATION SCATTERED RADIATION

CROSS-REFERENCE TO RELATED APPLICATIONS

The present application is a continuation-in-part of International Patent Application No. PCT/EP2013/064723, filed Jul. 11, 2013, which claims the benefit of European Patent Application No. 12 176 708.1, filed Jul. 17, 2012, both of which are hereby incorporated by reference herein in their entirety, including any figures, tables, or drawings.

FIELD OF INVENTION

The present invention relates to high-throughput nonlinear optical metrology and, in particular, to a device and a method for performing measurements and imaging with a high photon throughput using second harmonic generation (SHG) scattered radiation from a sample.

BACKGROUND

Many biological and chemical properties of nano- and micro-sized objects, such as particles, electrodes, implants, bubbles, droplets, viruses, micelles, liposomes and living cells are determined by processes occurring at the interface between the object and a medium surrounding or being in contact with the object. Examples of interface processes include the electrostatic current that flows through the outer membrane of a neural cell, the transport of proteins and reagents through a membrane, production processes inside organelles such as ribosomes and mitochondria, the uptake of oxygen in blood cells, or the formation of fibrous plagues responsible or related to Alzheimer's disease. These interface processes are usually confined to a 1 nm thick slab or layer that surrounds the object. Linear optical techniques are insensitive to interface processes and cannot be used for a determination of the properties of the interface processes of these objects.

Second-order nonlinear optical techniques are surface sensitive and ideally suited to image interface processes in isotropic media. Second harmonic generation (SHG) is a second-order nonlinear optical process, in which two photons (usually with identical frequencies and originating from the same laser beam) interacting via a nonlinear process with a material are effectively combined to form new photons with twice the frequency and half the wavelength of the initial photons. This process is a special case of sum frequency generation and unlike fluorescence the process is instantaneous. For isotropic materials the SHG process is forbidden in bulk media but allowed at interfaces. Apart from being sensitive to the structure of an interface, there is also a linear relationship between the emitted electric field and the electromagnetic potential. This includes the sensitivity for surface plasmons. Accordingly, probing a bulk liquid such as water with regard to a SHG process only gives rise to a very weak background signal arising from small fluctuations in the average isotropy of the structure. The generation of the background signal is commonly known as Hyper Rayleigh Scattering (HRS).

An overview of applications and experiments using a SHG scattering signal is given in [1]. In many previous experiments [1-7] the measurement setup included a femtosecond laser source emitting a single beam of laser pulses with a high repetition rate in a range from 80-90 MHz with a wavelength of 800 nm and pulse energies of up to 15 nJ. The SHG scattered signal was detected with a photomultiplier tube in the photon counting mode. In many cases chromophores were included in the samples to enhance the signal strength of the SHG scattered signal and improve the detection efficiency. Chromophores stimulate the emission of the SHG scattered radiation if the SHG photon energy matches one of the energy levels of the chromophore.

In a few studies [6, 8] no emission enhancing chromophores have been utilized. The intrinsic signal response of the interfaces was directly measured, but the detected SHG signal was very low. A corresponding experiment published in [6] reports about the detection of SHG scattered radiation from the surface of a dilute suspension of 100 nm polystyrene particles in water.

A global description of SHG microscopy is given in [9]. Most SHG microscopy applications rely on the detection of exogenous markers such as surface modifiable SHG active nanoparticles or endogenous bulk responses [10]. One example of detecting surface properties with SHG microscopy is the measurement of the membrane potential in dendritic spines using a SHG signal [11]. In this example chromophores were engineered to exhibit a membrane affinity so that they could be used to enhance the SHG signal from the membrane. In a number of cases endogenous structures have been investigated that exhibit a non-centrosymmetric structure and therefore give rise to allowed bulk SHG [12]. The instrumentation used for SHG microscopy is similar to that used for SHG scattering measurements and the more commonly employed confocal two-photon fluorescence microscopy. The experimental optical setup in most experiments typically includes an oscillator as a light source for excitation with a pulse repetition rate of more than 1 MHz and the pulse energies of the laser pulses are typically below 10 nJ. The excitation light is focused tightly onto a spot in the sample. The spot, or the sample, is then scanned and the SHG scattered signal is detected using a photon counting technique [9], so that the position of the spot is associated to the detected signal to then produce two- or three-dimensional image. Examples of a label-free surface sensitive SHG microscopy have been described as well. It was the object of these experiments to detect the surface chiral response of a patterned planar supported lipid bi-layer [13]. Wide-field SHG microscopes have also been devised [14][15] which eliminate the need for scanning. A common approach is to use a light source for excitation that also consists of an oscillator with a 75 MHz repetition rate and an intensified CCD camera [14], or a very low repetition rate (1 kHz, using a chirped pulse amplifier) and a regular CCD camera providing a poor photon throughput [15].

In second harmonic and multi-photon detection and imaging, varying the phase, polarization and temporal component of the excitation provides additional information regarding the sample under investigation. In scanning systems the phase is typically varied with a spatial light modulator (SLM) [16], while the polarization is changed with a wave plate, so that only one dimension of the nonlinear tensor representing the nonlinear properties of the sample can be addressed at a time, and it is not possible to modify the temporal component of the excitation. In certain wide-field configurations [15], in which the excitation beam is split into two beams, it is possible to address two dimensions of the nonlinear tensor and the temporal component.

U.S. Pat. No. 6,055,051 A refers to a method for determining surface properties of microparticles. Second harmonic generation (SHG), sum frequency generation (SFG)

and difference frequency generation (DFG) can be used for surface analysis or characterization of microparticles having a non-metallic surface feature. The microparticles can be centrosymmetric or such that non-metallic molecules of interest are centrosymmetrically distributed inside and outside the microparticles but not at the surface of the microparticles where the asymmetry aligns the molecules. The signal is quadratic in incident laser intensity or proportional to the product of two incident laser intensities for SFG, it is sharply peaked at the second harmonic wavelength, quadratic in the density of molecules adsorbed onto the microparticle surface, and linear in microparticles density.

WO 02 46764 A1 refers to methods of detecting molecules at an interface which comprise la-belling the molecules with a second harmonic-active moiety and detecting the labelled molecules at the interface using a surface selective technique. The disclosure also provides methods for detecting a molecule in a medium and for determining the orientation of a molecular species within a planar surface using a second harmonic-active moiety and a surface selective technique.

US 2010 031748 A1 discloses methods for detecting and evaluating the quality of protein crystals comprising subjecting a sample to second order non-linear optical imaging and detecting the second harmonic generation signal.

EP 07 40156 A1 relates to the use of nonlinear optical methods of surface second-harmonic generation and sum-frequency generation to detect immuno and enzyme reactions and nucleotide hybridisation.

In the majority of applications in which SHG signals have been used including SHG scattering experiments and SHG microscopic measurements chromophores such as fluorescent dyes, intrinsic or genetically modified proteins, quantum dots, and nanoparticles are utilized as beacons to enhance the strength of the SHG scattered light [1, 9].

However, the use of these photosensitive markers results in a low photo damage threshold of the sample material [15]. This in turn requires the use of low pulse energies of the exciting laser beam in order to avoid damages of the sample. In combination with low pulse energies high repetition rates of the laser pulses and a narrow laser focus are used in order to obtain sufficient signal strength that can be detected. Accordingly, to perform these measurements, pulse energies in the order of 0.1-1 nJ and repetition rates in the range MHz to GHz are typical for the laser sources [9]. For microscopy, these conditions often necessitate a confocal microscopy layout employing a narrow focus that is scanned across the sample. The need to scan the optical beam significantly limits the time resolution for imaging.

Most efforts to enhance the sensitivity of detection of SHG scattered signals either followed a direction to design and apply more efficient chromophores being less prone to photo damage or having a higher quantum efficiency, or a direction to optimize the pulse energy and repetition rate of the laser pulses with regard to the photosensitive markers. The latter optimization strategy resulted in scanning systems with (1) higher repetition rates (if the chromophores were already saturated by the applied laser pulse energies) or in (2) lower repetition rates to reduce thermal effects [9][19][20][21]. A study has been performed on the role that polarization, numerical aperture (NA), and wavelength has on the generation of second harmonic signal in collagen fibers [22]. In the latter study, it was found that lowering the NA, i.e. increasing the size of the illumination spot, decreases the signal. Other efforts relied on using a wide-field geometry with an accustomed high repetition rate (~80 MHz) [14], or with a low repetition rate (<10 kHz) yielding a poor photon throughput [15]. Therefore, none of the previously mentioned approaches have resulted in a significantly increased photon throughput and have a reduced photon damage risk.

BRIEF SUMMARY

Embodiments of the present application provide a device and a method for performing measurements using multiphoton and second harmonic generation (SHG) scattered radiation from a sample not being limited by the use of chromophores and a corresponding low photo damage threshold or a respective high repetition rate and delivering an increased photon throughput of the scattered SHG signal.

The method and apparatus for performing measurements using multiphoton or second harmonic generation (SHG) scattered radiation from a sample including a turbid (scattering) medium includes providing a beam of laser pulses from a laser source having high pulse energies and a repetition rate; splitting the beam of laser pulses into two or more partial beams and focussing and overlapping the partial beams on a sample including the turbid medium; and detecting multiphoton and second harmonic radiation scattered from the sample.

Preferably, the laser pulses have high pulse energies of more than 50 nJ and an optimum repetition rate, typically between 150 kHz and 1 MHz, such that a high photon throughput is obtained with a minimum risk of photo damage of the sample.

Due to the use of high pulse energies above 50 nJ and a repetition rate between 150 kHz-1 MHz in combination with wide field illumination, i.e. pulse energies in an energy regime above the energy regime of previous experiments, and the use of optimum repetition rates, in a regime different from previous experiments, the method permits the detection of interfacial processes on particles, bubbles, droplets, viruses, micelles, liposomes and living cells without any use of chromophores such as fluorescent dies, intrinsic or genetically modified proteins, quantum dots or nanoparticles as beacons or indicators of surface properties and still results in multiphoton or SHG scattered signals of sufficient strength. Therefore, the method permits a label-free observation of biological interface processes without labeling. The method is particularly suited to measure intrinsic interface properties of small objects in turbid media. A turbid medium is a medium that does not have temporal or spatial uniform dielectric properties so that light is scattered by it. The fluctuations in the average isotropy of a medium are classified as turbid when the linear dielectric properties deviate enough in time and space to cause light scattering.

Unlike fluorescence, the scattered second harmonic radiation of the method can be detected instantaneously. Furthermore, the time resolution will no longer be hindered by scanning since the spectra can be acquired with wide-field-imaging using a single shot per image of the spectrum. The wide-field-imaging enables a time resolution of the image acquisition of 1 microsecond. For most applications a scanning of the beam over the sample to form an image is not necessary.

Since the threshold of damage of the sample material is higher without any labels, a use of low pulse energies in combination with high repetition rates is not necessary. Because the efficiency of generation of multiphoton and second-harmonic photons is a square or higher order function of the pulse energy, but depends linearly on the repetition rate f, a significant improvement of detection throughput is obtained with respect to conventional methods due to the increased signal strength of the scattered radiation.

According to one embodiment, the laser pulses from the laser source have a repetition rate between 150 kHz and 1 MHz. More specifically, the repetition rates are selected from one of the ranges: 1 MHz to 600 kHz, 600 kHz to 300 kHz, and 300 kHz to 150 kHz.

According to yet another embodiment the pulse energies from the laser source are more than 50 nJ, more than 100 nJ, more than 1 µJ, more than 100 µJ. More specifically, the energy of the laser pulses is selected from one of the ranges between 50 nJ and 100 nJ, 100 nJ and 1 µJ, 1 µJ and 100 µJ.

According to a further embodiment, the laser pulses are focussed on the sample with a focus having a diameter of 10 µm, 100 µm, 500 µm or more or with a focus having a diameter in a range between these values. By enlarging the focus from ~10 µm to ~100 µm in diameter, the fluence can be kept low. For imaging the produced SHG or multiphoton light can be captured with an intensified and electron-multiplied CCD camera (EM-ICCD) enabling microsecond image acquisition times. Thus apart from increasing the detection throughput (for probing interfaces in-situ), much lower fluences can be used and fast tracking of nanoprobes is possible. In particular, due to the larger focus and the increased throughput of the embodiment it is no longer necessary to scan the samples for taking images. Images can be taken within short acquisition times in the range of microseconds. For example, acquisition times can be in the range between 1 µs and 1 s, in particular, can be 1 µs, 10 µs, 100 µs, 50 ms, 250 ms or 1 s, below 10 µs or above 1 s.

According to a further embodiment, the multiphoton or second-harmonic radiation that is emitted from the sample is detected by means of a gated photon counting technique. In this technique a photon counter may be coupled to the detector such as a photomultiplier or an EM-ICCD and can be used to electronically register or count the photons impinging on the detector only within defined, short time intervals which are preferably synchronized with the laser pulses of the pulse source. The intervals may include for example a time span of 1000 ns, 500 ns, 250 ns, 100 ns, 90 ns, 80 ns, 70 ns, 60 ns, 50 ns, 40 ns, 30 ns, 20 ns, 10 ns, 5 ns, or 1 ns or any other suitable time span. The beginning and/or the end of the photon counting time intervals may be controlled or triggered by laser pulses and preferably by the laser pulses split off from the pulse source beam used for exciting the sample. The gated photon counting technique is an efficient way to record light intensity of low level signals. Gating in conjunction with the pulsed light source permits to reduce the effective background count rate. It also permits to select fluorescence which is a non-instantaneous, delayed process from elastic second harmonic scattering, an instantaneous process.

The use of femtosecond pulses in a regime of high pulse energies and with a repetition rate in a regime of low repetition rates for the sample excitation in combination with a gated photon detection technique for the multiphoton or SHG photons according to this embodiment provides a further amended detection throughput and a higher quality of the detected signal.

According to still another embodiment, the beam is split into two or more partial beams being polarized.

According to yet another embodiment, the state of polarization of at least one of the partial beams is different from the state of polarization of at least one of the other partial beams.

According to yet another embodiment, the state of polarization of at least one of the partial beams is variable and is one of linear, circular or elliptical. Furthermore, according to yet another embodiment the pulses of at least one of the partial beams are timely delayed with regard to the pulses of the other partial beams. The delaying of the pulses can be achieved by a means such as a movable, in particular linearly displaceable, mirror that can be controlled to vary the length of the path of at least one of the partial beams. Spatial light modulators (SLMs) can also be used to modify the amplitude or the polarization or the phase or the delay of the pulses, or the temporal profile of the pulses.

The control of phase, polarization and time delay of the partial beams provide additional sensitivity with regard to particular surface characteristics such as surface chirality and energy flow. Accordingly, the detection efficiency for chiral surface constituents which have been shown to generate a significant amount of second harmonic signals can be enhanced. A chiral surface or a surface having chiral units absorbed on it will have non-zero second order susceptibility elements of the form $X\perp\|, \|'$ (where $\perp$ refers to the surface normal and $\|, \|'$ are two orthogonal tangential components). These second order susceptibility elements can be uniquely probed by using a crossed polarization scheme of the type PSP, PPS or SPP, wherein these polarization combinations refers to the specific polarization states of the scattered and incident beam, respectively. The first letter stands for the scattered light polarization state and the second and third for the polarization states of the incident beams. When the polarization vector is normal to the plane defined by the input and scattered beam, the polarization is referred to as S and when lying in the plane is referred to as P.

According to an embodiment, a system for detecting multiphoton and SHG scattered radiation from a sample including a turbid medium is provided. The system comprises a laser source outputting a beam of laser pulses; a beam splitter arranged to receive the beam of laser pulses and to split the beam of laser pulses into at least two partial beams; a sample on which the two partial beams are weakly focused and overlapped; a detector such as a photomultiplier or an EM-ICCD arranged to receive laser pulses from a laser source wherein the laser pulses from the laser source have a pulse energy of more than 50 nJ and a repetition rate of less than 1 MHz.

Due to a use of femtosecond laser pulses in a high energy regime and a repetition rate of the laser pulses in a regime of low frequencies the system allows a detection and imaging of interfacial processes of particles, electrodes, bubbles, droplets, viruses, micelles, liposomes and living cells with sufficient signal strength of the scattered SHG radiation without a use of markers such as chromophores to enhance the signal strength of the SHG scattered radiation. The system permits to efficiently detect the intrinsic interface response of any dielectric material. In particular, it permits a label-free measurement of biological interface processes.

According to another embodiment, a static wide field SHG or multiphoton microscope is used. It may comprise two weakly focussed beams that simultaneously illuminate a large portion of the sample at an angle. The angle is chosen such that (1) the intense fundamental beam does not damage the imaging objective lens, (2) allows for the analysis of eight possible polarization combinations which can be used to perform orientational analysis, as shown later and (3) highlights the presence of sub-micron sized structures. Detection is done by gating an EM-ICCD camera designed for low light applications. Although optimized for SHG imaging the system can easily be used for other types of microscopy, in both forward and epi detected geometries. The microscope may comprise other or additional components and modifications. The pulse length of the pulses in the beams may be in a range between 5 fs and 500 fs or more, limited to 10 microseconds.

According to yet another embodiment, a reciprocal phase-polarization-time control unit is provided in the system which is arranged to split the beam into two or more partial beams, which may have different polarization states. The reciprocal phase-polarization-time control unit comprises one or more of the components including a first telescopic system to decrease a beam diameter of a received beam, a beam displacer to split the beam into two collinear beams having orthogonal polarizations, a second telescopic system to increase the beam diameter of the received beam and their spatial separation, a cubic mirror, a time delay stage, and a spatial light modulator (SLM) operable in reflection mode. The SLM is configured in a way that the pattern of a beam received and displayed in the SLM controls the number of generated beams and their polarization. A temporal delay component of each of the at least two generated beams can be achieved by the time delay stage.

According to one embodiment the laser pulses from the laser source have a repetition rate of one of less than 1 MHz and more than 150 kHz, less than 600 kHz and more than 150 kHz, and less than 300 kHz and more than 150 kHz. More specifically the repetition rates are selected from a range selected from one of the ranges from 1 MHz and 600 kHz, 600 kHz and 300 kHz, and 300 kHz and 150 kHz.

According to yet another embodiment the pulse energies from the laser source are more than 50 nJ, more than 100 nJ, more than 1 µJ, more than 100 µJ. More specifically, the energy of the laser pulses is selected from one of the ranges between 50 nJ and 100 nJ, 100 nJ and 1 µJ, 1 µJ and 100 µJ.

According to a further embodiment, the laser pulses are focussed on the sample with a focus having a diameter of 10 µm, 100 µm, 500 µm or more or with a focus having a diameter in a range between these values. For imaging the produced multiphoton or SHG light can be captured with an EM-ICCD camera enabling microsecond frame rates. The emitted multiphoton or SHG signal scales at least quadratically with the pulse energy, while the fluence scales linearly with the pulse energy. By enlarging the focus from ~500 nm in diameter as used commonly in point scanning to ~10-500 µm, the fluence can be reduced. Thus, apart from being more sensitive (for probing interfaces in-situ) and enabling fast time tracking of nanoprobes, lower photodamages are achieved.

According to one embodiment, the detector is arranged to detect laser pulses with a gated photon counting technique. In this technique a photon counter is coupled to the detector such as a photomultiplier or a an EM-ICCD and is adjusted to count the photons impinging on the detector only within defined, short time intervals. The beginning of the time intervals may be synchronized with the laser pulses from the pulse source by using the pulses, and preferably their leading edges for triggering of the photon counting. The time intervals may include, for example, a time span of 999 ns, 500 ns, 250 ns, 100 ns, 90 ns, 80 ns, 70 ns, 60 ns, 50 ns, 40 ns, 30 ns, 20 ns, 10 ns, 5 ns, 1 ns or any other suitable time span.

The use of a gated photon counting technique in combination with the laser pulses of high energy and a low repetition rate of the femtosecond laser pulses of the system provides an optimized detection of second-harmonic scattered radiation from intrinsic samples. Low photo damage thresholds related to a use of photosensitive markers can be avoided. Instead, high-pulse energies of more than 50 nJ and repetition rates of less than 1 MHz can be applied permitting reasonable signal strengths without a use of any chromophores. The gated photon counting in conjunction with the pulsed light source reduces the effective background count rate and hence improves the signal strength and quality.

According to another embodiment, the system comprises a means to vary the path length of at least one of the two partial beams with regard to the other partial beam. This means can be implemented by a movable mirror.

According to yet another embodiment, the beam splitter is arranged to split the beam of laser pulses into two partial beams being polarized, wherein the state of polarization of one of the partial beams is different from the state of polarization of the other partial beam.

Controlling the polarization and time delay results in additional sensitivity of the system enhancing the detection of chiral surface constituents generating a significant amount of second-harmonic signals.

According to still another embodiment, the system comprises a means to vary the state of polarization of at least one of the partial beams to one of linear, elliptical, or circular polarization.

According to yet another embodiment, the sample includes one or several of a turbid medium, a particle, a bubble, a droplet, a virus, a micelle, a liposome and a living cell.

BRIEF DESCRIPTION OF DRAWINGS

FIGS. 6A-6B show a comparison of samples with a detection angle of 30° degrees, an acquisition time of 10 s, a repetition rate of 200 kHz, laser power in front of the focusing lens of 118 mW, and PP polarization, wherein FIG. 6A shows a SHG signal response from the surface of PS particles (0.026 v.v %, and a diameter of 500 nm), and 4 nm gold nanoparticles, and FIG. 6B shows a comparison of signal strengths for liposomes (0.075 v.v %), nanoparticles (8 nm, 12 µg/ml), and polystyrene particles (0.026 v.v %, diameter 500 nm).

FIGS. 7A-7B show wide field and phase contrast and second harmonic (FIG. 7A) images taken of cultured mouse brain neurons.

DETAILED DESCRIPTION

The following non-limiting exemplifying embodiments are described with respect to the Figures.

Figure 1A:
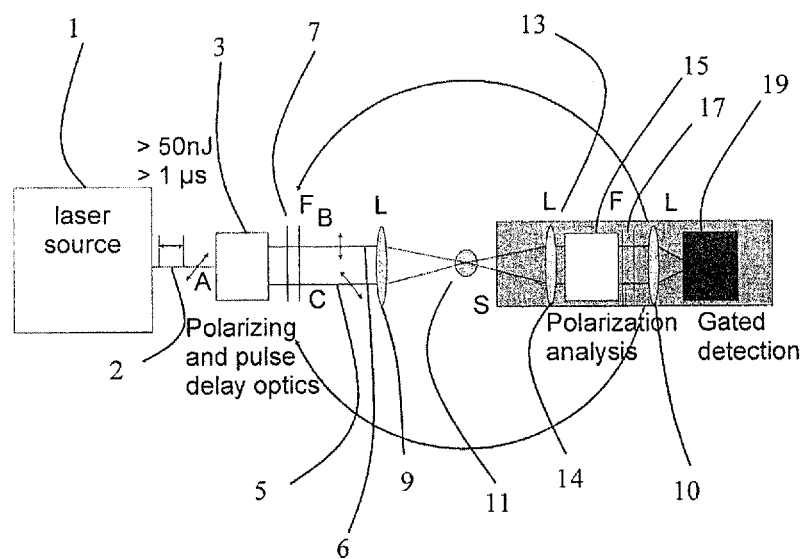
FIG. 1A shows an experimental setup for measuring SHG scattered radiation from a sample including a turbid medium, in accordance with an embodiment of the subject invention.

An example of an experimental optical setup for measuring second harmonic generation (SHG) scattered radiation from a sample is presented in FIG. 1A. It includes a laser source 1. In particular, the laser source is a laser system (Pharos, Light Conversion) delivering a beam 2 of femtosecond pulses with a repetition rate of f<1 MHz, and pulse energies >50 nJ. The beam 2 is split by a polarizing beam splitter 3 into a first partial beam 5 and a second partial beam 6. The partial beams have different states of polarization, preferably perpendicular states of polarization. Furthermore, means (not shown) that are arranged to controllably vary the path length of at least one of the partial beams 5, 6 and means to control or change the state of polarization of at least one of the partial beams 5, 6, and means to control or change the phase of at least one of the partial beams 5, 6, and means to control or change the temporal profile of at least one of the partial beams 5, 6 such as a polarizer, polarization modulator, half-wave plate or spatial light modulator may be included in the system. Both partial beams 5, 6 are collimated, passed through filters 7 and focussed with the same optic, in particular lens 9, on a sample 11. Appropriate filters 7 are filters that block the transmission of irradiation with wavelengths other than that of the light source 1. The radiation scattered from the sample 11 is focussed in a detector arrangement 13. The detector arrangement 13 includes a lens 14 to collect and collimate the scattered light, a polarizer 15 for selecting the polarization state of one of the two partial beams 5, 6, a filter 17 that allows the transmission of radiation having a wavelength half of that of the incident beam and a lens 10 to focus the light on a gated detection means 19. The experiments described with regard to FIGS. 3-6A-6B have been conducted with this optical setup.

Figure 2:
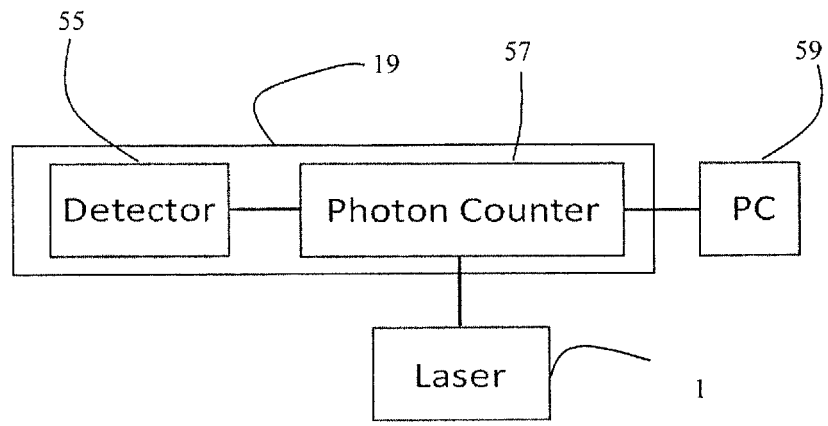
FIG. 2 shows a schematic representation of the gated detection means used in the experimental setup.

In the gated detection means 19 schematically shown in FIG. 2 a photomultiplier can be used as the detector 55. Alternatively, an EM-ICCD camera with a spectrometer (not shown) can be used as the detector 55 providing signal measurements with spectral dispersion. The gated detection means 19 includes a photon counter 57 that is coupled to the detector 55 and that permits to count photons within defined, preferably short time intervals. The photon counter 57 is controlled by a computer 59 and the photon counting is preferably synchronized with the pulsed light source. In particular the photon counting is triggered by the pulses emitted by the source 1. Gating in conjunction with the pulsed light source is used to reduce the effective background count rate and provides signals of better quality having less noise. In particular, the gated photon counting method is of advantage when low laser pulse repetition rates are used, since the effective detection intervals can be shortened compared to the time intervals between laser pulses. Hence, the background count rate can be reduced. Preferably, the gating time width is narrower than 100 ns and can be for example 100 ns, 90 ns, 80 ns, 70 ns, 60 ns, 50 ns, 40 ns, 30 ns, 20 ns, 10 ns, 5 ns, or 1 ns.

The detector 13 is positioned on a swivelling arm (not shown) that can be rotated about almost 360° around the sample 11 in the plane of the figure and hence adjusted to almost any scattering angle.

The possibility of controlling polarization and time delay of the partial laser beams 5, 6 brings additional sensitivity with respect to surface chirality and energy flow in some experiments. Using different polarization combinations allows for the probing of different tensor components of the second-order susceptibility. These tensor components can originate e.g. to chiral constituents or crystallites. By delaying the laser beams different processes can be probed. The time delay can be used to change the time overlap between the pulses. As an example, overlapping beams with P and S polarization under an angle can give rise to SPS, SPP, PSP, PSS polarization combinations if the time delay of both pulses is matched. The signal generated by the individual beams (PPP, SSS, SSP, PPS) is always generated regardless of the time delay.

The device operates in combination with a software for analysis of the data. This software includes modules for predicting scattering patterns as well as modules for the analysis and suppression of fluctuations by means of correlation functions (dynamic nonlinear light scattering, see [23]). The software may also contain a compressive sensing algorithm that can be used in a feedback loop in combination with a digital mirror device placed at the location of 15. The above improvements are equally applicable to second harmonic imaging. Acquired data that are presented below show the significant improvement over state of the art methods.

Figure 1B:
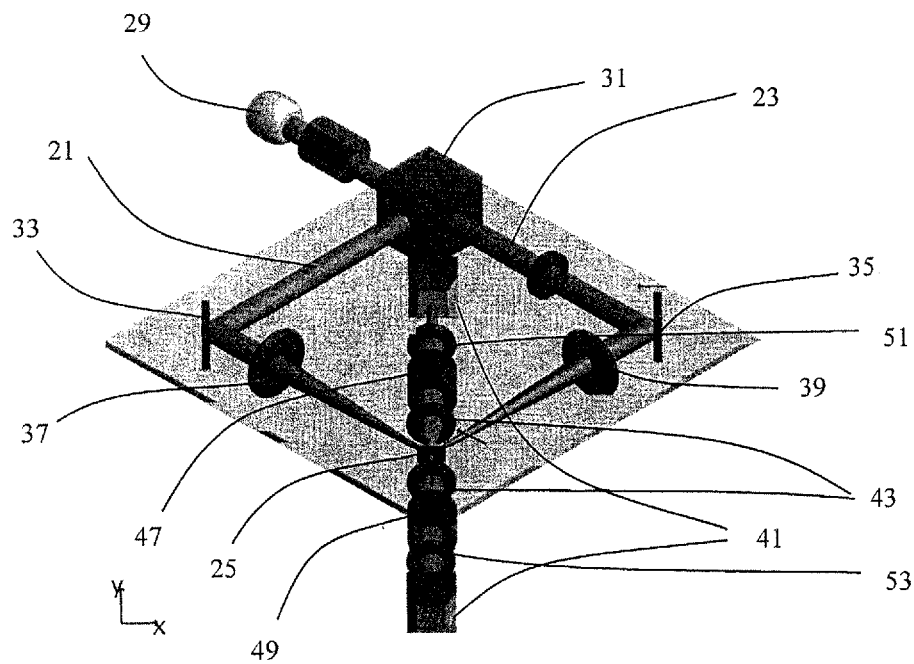
FIG. 1B shows an optical scheme of a SHG and multiphoton microscope with a two beam configuration.

Alternatively, the experiments were carried out with a static wide field SHG and multiphoton microscope as shown in FIG. 1B. The SHG microscope comprises two loosely focused 190 fs, 1030 nm, 10-200 kHz, 1-1000 nJ beams 21, 23 that simultaneously illuminate a large portion of a sample 25 at an angle. The angle is chosen such that (1) the intense fundamental beam 21, 23 does not damage the imaging objective lens 27, (2) allows for the analysis of eight possible polarization combinations which can be used to perform orientational analysis, as shown later and (3) highlights the presence of sub-micron sized structures. The two beams 21, 23 are generated by splitting a beam of laser pulses emitted from a laser 29 with a non-polarizing beam splitter 31. Each of the beam paths includes a mirror 33, 35 reflecting the respective beam 21, 23 towards the sample 25, wherein at least one of the mirrors 33, 35 is displaceable and can be used as a variable delay in the beam path. Furthermore two low NA lenses 37, 39 are used to focus the beams 21, 23 on the sample 25. Detection is done by gating an EM-ICCD camera 41 optimized for low light applications. The optimized camera setup includes two high NA lenses 43 for collecting the SHG light which are positioned on opposite sides of the sample and two EM-ICCD cameras 41 behind the high NA lenses 43. Between the high NA lenses 43 and the EM-ICCD cameras 41 a respective polarization state analyser 47, 49 and tube lens 51, 53 are positioned. Although optimized for SHG imaging the system can easily be used for other types of microscopy, in both forward and epi detected geometries. The experiments described with regard to FIGS. 7A-7B, 8A-8F, 9A-9E and 10A-10D have been conducted with this SHG microscope.

Figure 1C:
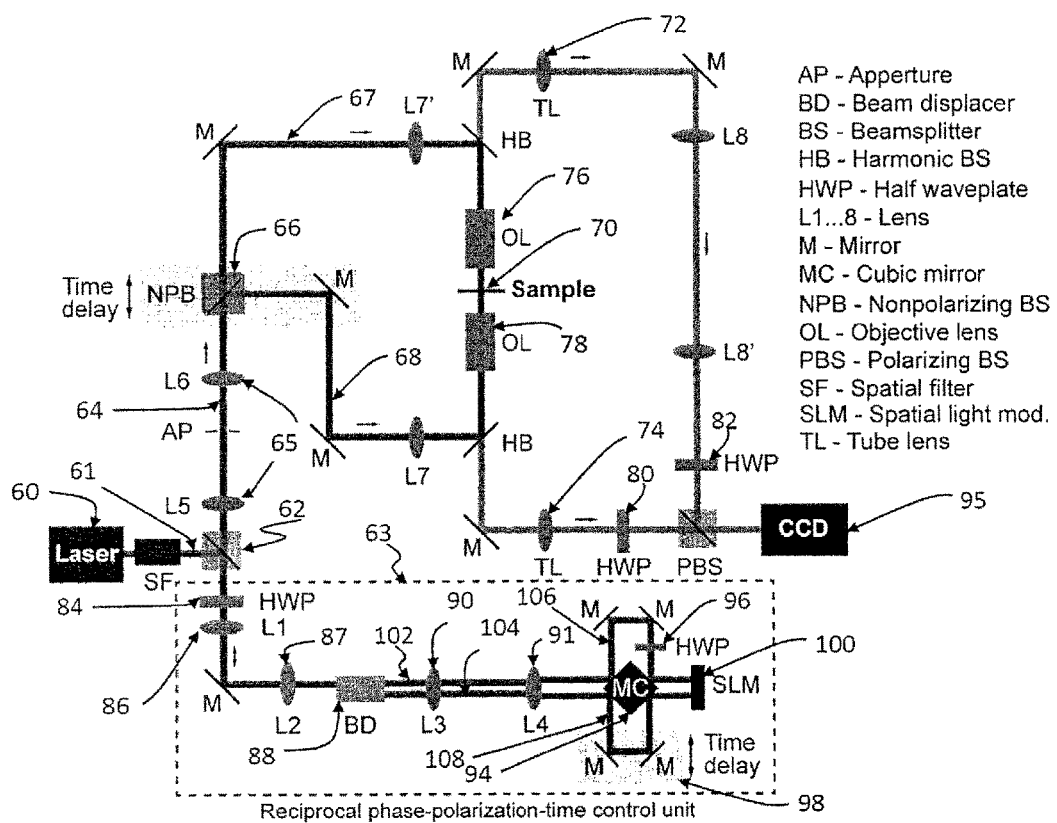
FIG. 1C shows an optical scheme of a SHG and multiphoton microscope capable of generating multiple beams, where a single beam is shown for simplicity.

FIG. 1C shows an embodiment of an SHG microscope with a multiple beam configuration. It comprises a laser source 60 which can be similar to the laser source described above with regard to FIG. 1A. A beam 61 emitted by the laser source 60 is directed by a beam splitter 62 into a reciprocal phase-polarization-time control unit 63 that is configured to split the beam 61 into two or more composite partial beams 64, which may have different polarization states. The composite partial beams 64 pass through a telescopic lens system 65 to then be split by a beam splitter 66 into two paths 67, 68. One path 67 is intended to illuminate a sample 70 in transmission and the other path 68 is intended to illuminate the sample in reflection. Each one of these paths 67, 68 contains a tube lens 72, 74 and high NA lenses 76, 78. The sample 70 is then placed in between the high NA lenses 76, 78. The sample 70 is illuminated by a large spot in a wide-field mode. The spot can range in sizes between 10 and 100 micrometers. The detection is done in transmission and epi configuration with an imaging spectrometer and an EM-ICCD camera 95. The image can be acquired with the EM-ICCD camera 95 in one or more of the following configurations: Acquisition in transmission on one or both sides of the sample 70, and/or acquisition in reflection on one or both sides of the sample 70. Between the high NA lenses 76, 78 and the imaging spectrometer a respective polarization state analyser and the tube lens 72, 74 are positioned. In this case the polarization state analyser comprises a broadband half wave-plate 80, 82 and a broadband polarizing beam splitter. The imaging spectrometer can be set in imaging-only mode to produce an image of the sample 70 or in spectroscopy mode to measure the spectra of the sample 70. Instead of the EM-ICCD camera 95 also other detectors like a phototube with a spectrometer, a Streak camera, a CCD camera or another suitable detector can be used.

The reciprocal phase-polarization-time control unit 63 comprises a half wave plate 84, a first telescopic lens system 86, 87, a beam displacer 88, a second telescopic lens system 90, 91, a cubic mirror 94, a half wave plate 96, a time delay stage 98, and a spatial light modulator (SLM) 100 that operates in reflection mode. An SLM consists of an array of small optical elements (e.g. mirrors, liquid crystals (LC)) that can be adjusted indivually to modify the phase and/or amplitude of an optical beam [25]. The array of small optical elements or a portion thereof can be adjusted in a way that a two-dimensional diffraction pattern for an incident beam is generated.

The beam displacer 88 (Thorlabs) splits the incoming beam 61 into two collinear partial beams 102, 104 having orthogonal polarizations and the same intensity. The spatial separation of the two collinear partial beams 102, 104 is defined by the length of the beam displacer 88. An important limitation of the system is thus given by the diameter of the incoming beam 61. If the diameter of the incoming beam 61 is larger than the expected separation, the two collinear partial beams 102, 104 overlap making their individual manipulation impossible. To avoid this limitation, the diameter of the incoming beam 61 is first reduced in size by the first telescopic lens system 86, 87 and then increased by the second telescopic lens system 90, 91. The latter increases the diameter of the two collinear partial beams 102, 104 and the separation between them. The increased diameter reduces the fluence incident on the SLM 100 to avoid damage, and the increased separation facilitates the redirection of the beams using the cubic mirror 94 into two different paths 106, 108. One path 106 contains a half wave plate 110 that rotates the state of polarization to be along the active axis of the SLM 100. A conventional delay stage 112 is placed in the other path 108 to induce a temporal delay of the excitation beam at the sample 70. The two paths 106, 108 of the two collinear partial beams 102, 104 are directed via respective mirrors M and the cubic mirror 94 into the SLM 100. The SLM 100 then modulates the phase and/or amplitude of at least one of the two collinear partial beams 102, 104. One half of the SLM 100 is destined to modulate one of the partial beams 102, whilst the other half is intended to modulate the other partial beam 104.

The SLM can be one of many instruments. In this implementation we use an array of $>2 \cdot 10^6$ liquid crystals (LCs) that are mounted on a mirror. By varying a voltage connected to each LC seperately the optical path length of the light through each one of the LCs can be controlled seperately. In this way a beam can be reshaped into two beams or more with different polarization components. Rings and other beam shapes can be produced as well. If the SLM 100 is set to neutral (idle) mode, the two collinear partial beams 102, 104 are reflected back along their incident paths 106, 108 to then be recombined by the beam displacer 88. The latter conditions result in a single composite beam 64 exiting the reciprocal phase-polarization-time control unit 63. For the reciprocal phase-polarization-time control unit 63 to produce two or more composite partial beams 64, the phase and/or amplitude of the two collinear partial beams 102, 104 must be modulated by a binary, blazed, or sinusoidal diffraction pattern generated by adjusting the voltages applied to at least a portion of the LCs in the SLM 100. The diffraction pattern splits the collinear partial beams 102, 104 into two or more diffracted beams, namely diffractive orders. The diffracted beams propagate back following the path 106,108 of the collinear partial beam 102, 104 from which they originated. The beam displacer 88 then recombines the diffracted beams from the two collinear partial beams 102, 104 to create two or more composite partial beams 64.

For example, to produce two composite partial beams 64, the diffraction pattern generated in the SLM 100 can be a sinusoidal diffraction grating that modulates the phase, or the amplitude or both. The sinusoidal diffraction grating splits the collinear partial beams 102, 104 into two diffracted beams each (four in total), which are then recombined by the beam displacer 88 to from two composite partial beams 64. The number of composite partial beams 64 thus depends on the number of diffracted beams produced at the SLM 100. The composite partial beams 64 can be propagating along different geometrical planes, namely the diffraction plane. In the previous example, the orientation of the diffraction grating defines the plane of propagation of the diffracted beams and hence of the composite partial beams 64. The diffraction pattern is chosen by the user to define the number, plane of propagation, and amplitude of the composite partial beams 64. It is possible to use one- or two-dimensional diffraction gratings as diffraction pattern. When using two-dimensional gratings, the diffracted beams generated at the SML 100 can propagate along different geometrical planes.

The number, diffraction plane, and amplitude of the diffracted beams depend on the chosen diffraction pattern, which is restricted by the type of SLM 100 used (which can be phase only, amplitude only, or both phase and amplitude [25]. In the case of a Phase-Only-SLM 100, the phase of the incident light is spatially varied across the beam by adjusting the optical path length followed by the light as it travels through the liquid crystal units of the SLM 100. The polarization of the composite partial beams 64 depends on the amplitude modulation of the two collinear partial beams 102, 104. The amplitudes of each one of the two collinear partial beams 102, 104 define the magnitude of the polarization components of the composite partial beams 64. For example, if the amplitude of one of the partial beams 102 is set to zero, the composite partial beams 64 have the polarization of the other partial beam 104. If the amplitude is set to equal in both partial beams 102, 104, the magnitude of the polarization components of the composite beam is equal, resulting in a polarization oriented at forty-five degrees with respect to the polarization of the partial beams 102, 104. The diffraction pattern can be chosen such that the diffracted beams have different amplitudes, and hence produce two or more composite partial beams 64 with different states of polarization.

The diffraction plane of the diffracted beams depends on the diffraction pattern and can be any plane perpendicular to the SLM plane 100. It is possible, for example, to generate with a two-dimensional diffraction pattern two composite partial beams 64 propagating on a plane and two more propagating on an orthogonal plane (as in a cross). The intensity distribution of the composite partial beams 64 can also be modified by applying amplitude-modulating masks on the two collinear partial beams 102, 104 using the SLM 100. The amplitude-modulating masks comprise a diffraction pattern that is capable of varying spatially the amplitude of the collinear partial beams 102, 104. Moreover, the reciprocal phase-polarization-time control unit 63 is configured so that the group velocity dispersion imposed on the pulses of the collinear partial beams 102, 104 in the SLM 100 is such that the pulse is compressed to its theoretical minimum.

Figure 1D:
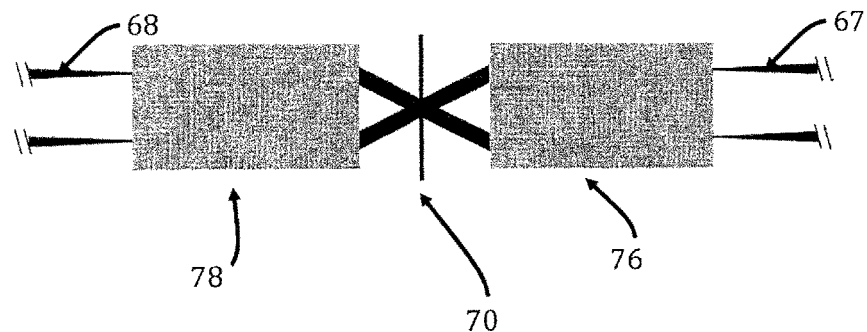
FIG. 1D shows a magnification of the high numerical aperture lenses of the SHG and multiphoton microscope capable of generating multiple beams exemplifying the case of the two beam configuration.

The SLM 100, the exit (and entrance) plane of the reciprocal phase-polarization-time control unit 65, and the sample plane of the microscope are conjugate to each other, i.e. the SLM 100 is imaged onto the exit plane of the reciprocal phase-polarization-time control unit 63 and onto the sample 70. This means that when two or more composite partial beams 64 are generated by the reciprocal phase-polarization-time control unit 63, the composite partial beams 64 enter the high NA lenses 76, 78 off-centred (see FIG. 1D). Consequently, the composite partial beams 64 exit the high NA lenses 76, 78 at an angle and overlap at the focal plane of the high NA lenses 76, 78, which is the plane where the sample 70 is placed (see FIG. 1D).

The angle of incidence of the composite partial beams at the sample 70 depends on the spatial period of the diffraction pattern (which is controlled by applying a voltage pattern across the LC array in the SLM 100). For diffraction patterns with short spatial periods the angle between the composite partial beams is larger, while for diffraction patterns with long spatial periods the angle is smaller. Moreover, interference patterns can be observed at the sample depending on the angle between the composite partial beams due to the temporal properties of the laser beam. The interference pattern is less pronounced when the opening angle is increased. For larger opening angles, the sample 70 is illuminated with a spot that does not display an interference pattern. The interference pattern can be used to obtain depth sectioning as in structured illumination techniques [26].

Similar to the embodiment of FIG. 1B, eight possible polarization combinations are allowed which can be used to perform an orientational analysis. In addition, the possibility of generating multiple beams propagating along multiple planes allows for more complex polarization combinations. For example, four beams propagating along two orthogonal planes, two beams per plane, with a polarization along their plane of propagation allows to probe SPP and SSS or PPP and PSS simultaneously. Moreover, measuring with multiple beams propagating along multiple planes can enhance the presence of the longitudinal component of the polarization (i.e. the component along the direction of propagation) with respect to the transverse components (i.e. the components orthogonal to the direction of propagation: on the plane of the sample). The latter configuration allows one to access more efficiently the longitudinal elements of the nonlinear tensor that represents the nonlinear properties of the sample 70 under investigation.

The transverse optical resolution of the system in FIG. 1C can be similar to that of a nonlinear confocal scanning microscope. When using multiple beams propagating along multiple planes, the sample 70 is illuminated at different angles along different planes. The SHG and multiphoton light generated from each angle and plane carries information regarding the structure of the sample. The image formed at the EM-ICCD 95 then contains the collective information from the different angles and planes. The latter configuration results in a transverse optical resolution greater than in a conventional wide-field systems based on Koehler illumination and similar to a nonlinear confocal scanning microscope.

Experimental Results:

Experiments were performed using SHG scattering to measure the surface response of materials. In the present studies and in the absence of adsorbed molecules such as chromophores the SHG signal is a second-order response from a sample surface composed of a structural and a charge contribution such as ions that are in proximity to the surface.

In those experiments, a light source providing 190-fs pulses at a fundamental wavelength of 1030 nm was used with a tunable repetition rate ranging between 1-200 kHz. The incident beam was focused into a cylindrical cell including the sample with a diameter of 0.4 cm. SHG scattered photons were detected in the transmitted direction at variable scattering angles using gated photon counting. Filters were used to separate the SHG scattered photons from the background signal of the fundamental laser mode and other background signals. The measured data included SHG scattered radiation from polystyrene (PS) particles (500 nm diameter), liposomes (100 nm diameter) dispersed in water, and gold nanoparticles (8 nm diameter) in water and the Hyper Rayleigh Scattering (HRS) background signal from the water. The SHG signal from the scattering interface was obtained by subtracting the HRS response from the total SHG signal response.

As mentioned above, in most earlier experiments particle interfaces are probed by means of chromophores that absorb exciting light on the surface. For a few measurements for which a non-resonant label-free response was reported, the signal was very low and close to the detection limit. Therefore all test measurements have been performed using the non-resonant surface response. This response has been reported in [6]. Comparisons will be made with respect to that study.

The following test experiments were performed:
(i) Verification of the measurement of true surface SHG signals; (ii) Performance test and comparison to previous instruments; and (iii) Test of different materials.

(i) The verification of the measurement of surface SHG signals included proving that the non-resonant surface response of the PS particles was measured. The sample used consisted of polystyrene (PS) beads with a diameter of 500 nm. It was checked that: (a) the SHG signal varied as a square function of the input intensity; (b) the signal depends linearly on the particle density; (c) there is no contribution from the sample cell windows as a source for the SHG signal; (d) the SHG signal occurs exactly at the double frequency of the fundamental mode of the exciting laser; (e) and that the polarizations of the SHG signal and the HRS signal are different.

Figure 3:
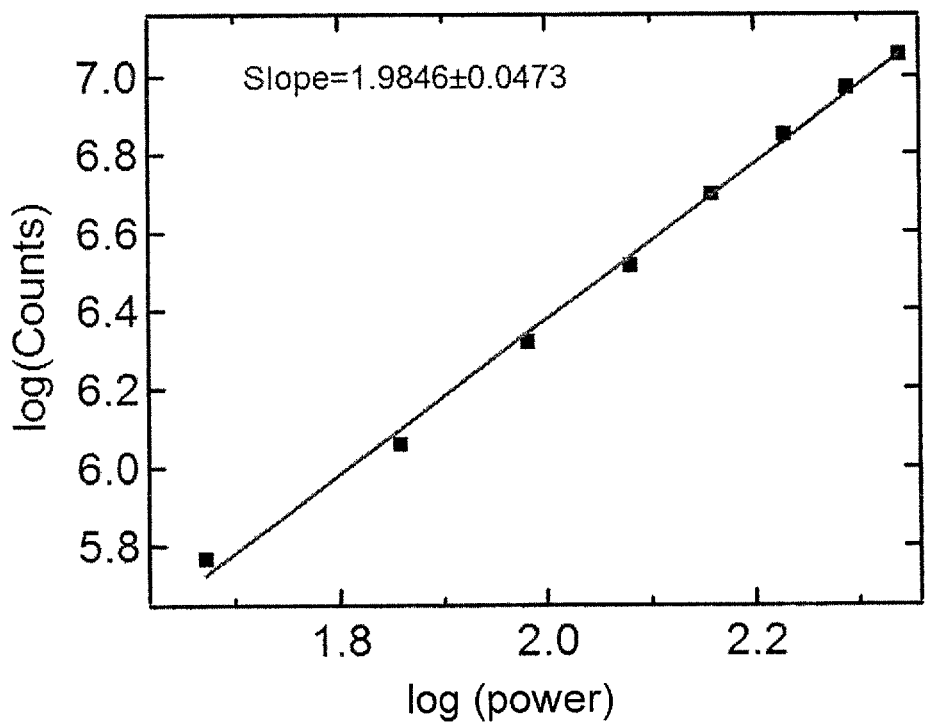
FIG. 3 shows the power dependence of a SHG scattered signal from a solution with PS beads with a 0.026 v.v % and a diameter of 500 nm, PP polarization combination and a repetition rate of 200 kHz. The power is measured in front of the focusing lens in mW, wherein the scattered light was detected at 30 degrees with an angle of acceptance of 20 degrees and a data acquisition time of 10 s.

Regarding (a) it was verified that the signals from all samples displaying a SHG signal exhibit a square function dependency on the incident fundamental intensity which confirms that the signal is a SHG scattered signal. FIG. 3 highlights this behavior for a sample including an aqueous solution of 500 nm diameter PS particles.

Figure 4:
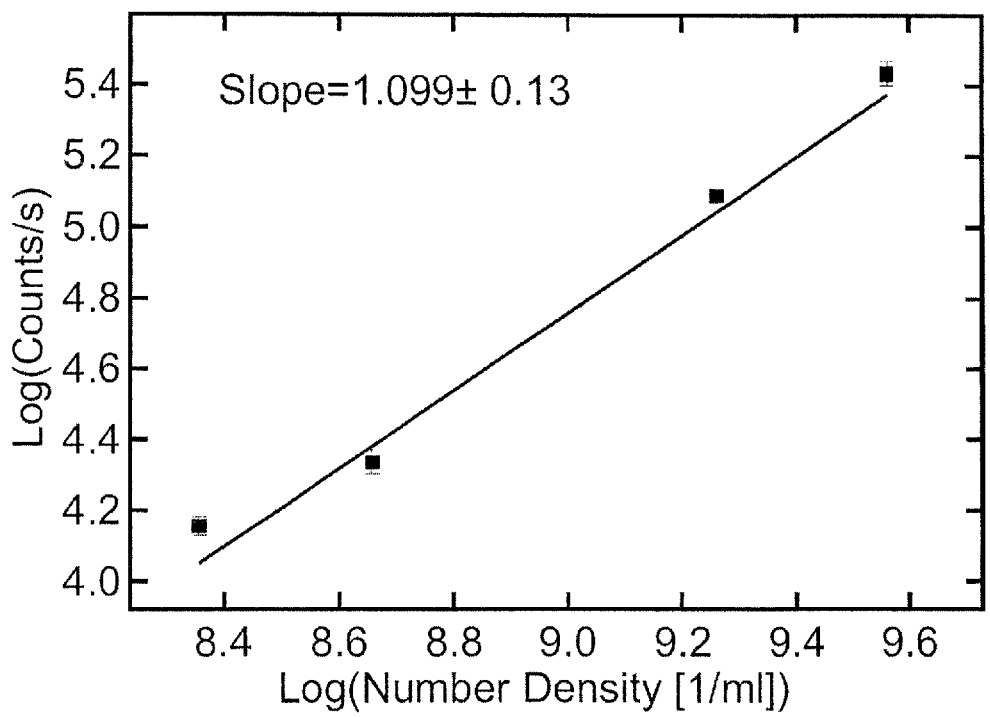
FIG. 4 shows the intensity of a SHG signal from aqueous solutions of PS particles with diameters of 500 nm, PP polarization combination (PP polarization combination refers to the specific polarization states of the scattered and incident beam respectively. The first letter stands for the scattered light polarization state and the second for the polarization state of the incident beam. When the polarization vector is normal to the plane defined by the input and scattered beam, the polarization is referred as S and when lying in the plane is referred as P) and a repetition rate of 200 kHz as a function of particle density, wherein the laser power measured in front of the focusing lens was 118 mW, and the scattered SHG signal was detected at 30 degrees with an angle of acceptance of 20 degrees and an acquisition time of 10 s.

Regarding (b) the functional dependency of the intensity of the SHG signal on the density of scatterers in the solution was investigated. This was done to probe the incoherent nature of the scattering process. FIG. 4 illustrates the obtained results for an aqueous solution of 500 nm PS particles over a range of particle densities of 1-10 $10^9/cm^3$. The observed linear dependency indicates that the nanoparticles do not exhibit coherent interactions, since in this case, a nonlinear dependency of the SHG signal on particle density would have resulted.

Regarding (c) the focus of the incident beam was varied and sample cells of different optical path lengths have been used. Thereby, it could be shown that the SHG scattered signal did not originate from either the input window or output window of the cells. This was further verified by using a liquid-jet produced in a pump driven flow system. In this experiment the sample cell was replaced by a liquid jet produced in a pump driven flow system. In this way a generation of SHG radiation that is generated by the cell windows was avoided.

Regarding (d) a β-BBO crystal was placed in the path of the fundamental mode and the spectrum was recorded. The SHG spectrum obtained with the β-BBO crystal was identical to the SHG spectrum obtained with the sample. This proves that the SHG signal and no fluorescence was measured.

Regarding (e) it could be confirmed in a measurement that the polarization of a SHG signal from the PS particle surface was different from the polarization of the HRS from water in accordance with theory (e.g. [6]).

Figure 5:
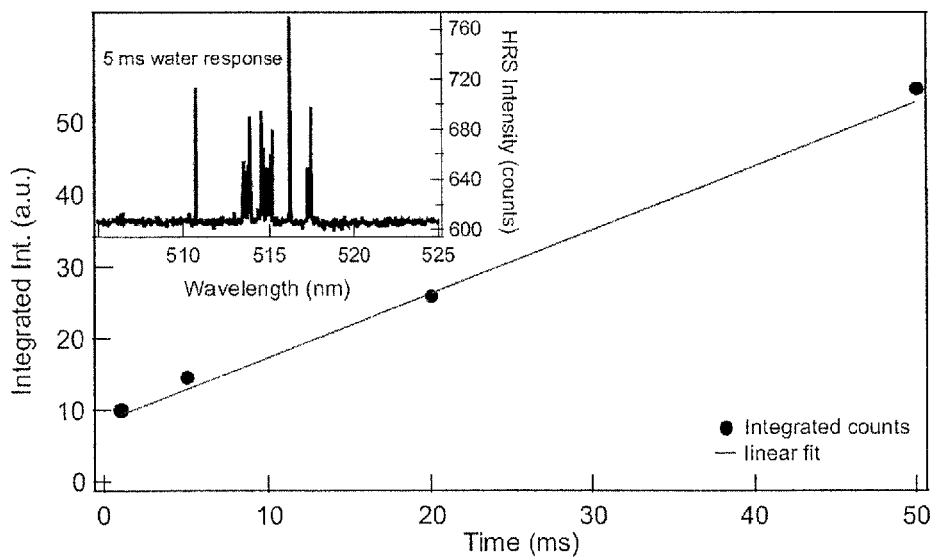
FIG. 5 shows the integrated intensity of Hyper Rayleigh Scattering from pure water as a function of exposure time, wherein the inset shows the response for a time lapse of 5 ms (i.e. 1000 laser shots); the angular resolution was 1.4° degrees and the scattering angle was set to 51.4° degrees.

Furthermore, the performance of the device was compared with the experiments published in [6]. The result is shown in FIG. 5.

The acquisition time limit at 200 kHz is <1 ms for the HRS response of water. This threshold time for detecting a signal is 500 times shorter than what is reported in literature. Comparing the signal response of water obtained by the present measurement to that in [6], an improvement of the signal to noise ratio of a factor of 5 was observed. If the ultra-low response of water can be measured with a 1 ms time resolution, then it is expected that the weak response of interfaces can be recorded on time scales important for biological processes.

Different materials have been tested with the experimental setup shown above. Spectra of 500 nm PS particles in water and 8 nm gold nanoparticles are presented in FIG. 6A. The signal from the polystyrene particles reflects the exact SHG spectral response of the exciting pulses, while the gold nanoparticles exhibit a broader spectrum. The broadening is due to the excitation of a plasmon resonance. A comparison of the signal strength for three different samples is shown in FIG. 6B, in which the gold nanoparticles and the polystyrene beads are compared with 100 nm liposomes (composed of POPG). Comparing this data to data in literature (for polystyrene Ref. [6], for gold nanoparticles Ref. [24], and for liposomes Ref. [8]), shows a marked increase in device performance.

For the imaging experiments the scheme of FIG. 1B was used with forward detection. We measured: (1) label-free images of human ovarian cancer cells, mammalian neurons, and human epithelial cancer cells, (2) SHG nanoparticles (30 nm $BaTiO_3$, and 100 nm $KNbO_3$) diffusing in water and in cells, (3) voltage related SHG signal on microelectrodes, (4) real time electrolysis reactions of water on those microelectrodes, (5) membrane potential images on living neurons.

Figure 8A:
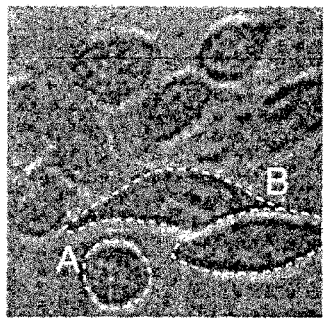
FIGS. 8A-8C show phase contrast images.
Figure 8B:
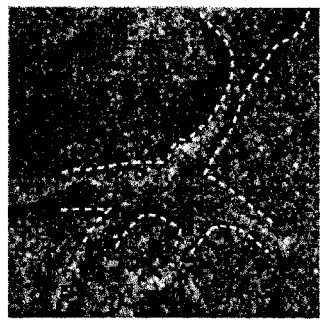
Figure 8C:
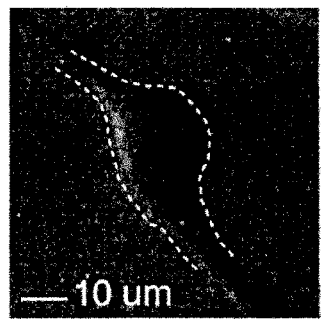
Figure 8D:
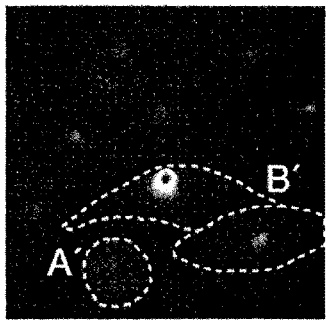
FIGS. 8D-8F show corresponding SHG images of living human ovarian cancer cells (FIGS. 8A, 8D), axons of living mammalian neurons (FIGS. 8B, 8E), and epithelial cancer cells (FIGS. 8C, 8F).
Figure 8E:
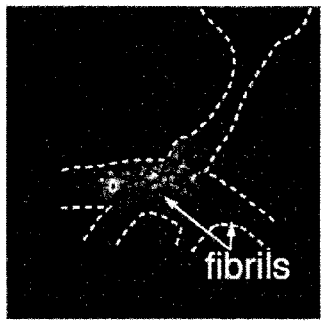
Figure 8F:
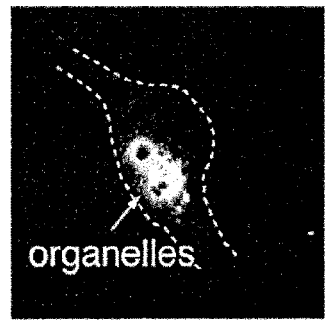

FIGS. 8A-8C show phase contrast images and FIGS. 8D-8F show corresponding SHG images of further samples. The images have been taken from living human ovarian cancer cells (FIGS. 8A, 8D), axons of living mammalian neurons (FIGS. 8B, 8E), and epithelial cancer cells (FIGS. 8C, 8F). The dashed lines are a guide for the eye. The SHG light originates from the different organelles in the cells that may have a different SHG emission depending on the state of their life cycle. Furthermore, the SHG images show that each cell type has a different SHG signature. The taking of those images is useful for cancer research or cell diagnostics. A label-free SHG imaging of single cells has not been reported before.

Figure 9A:
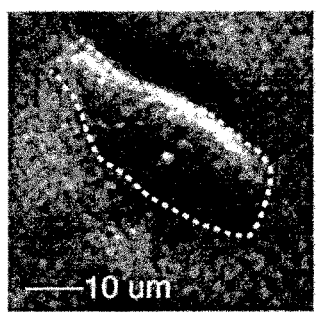
FIGS. 9A-9E show time resolved images of living cells including a wide field image (FIG. 9A) and a SHG image (FIG. 9B) of human epithelial cells, two particle tracks (FIG. 9C); and the determined mean square angular displacement (FIG. 9D) and spatial (FIG. 9E) displacement.
Figure 9C:
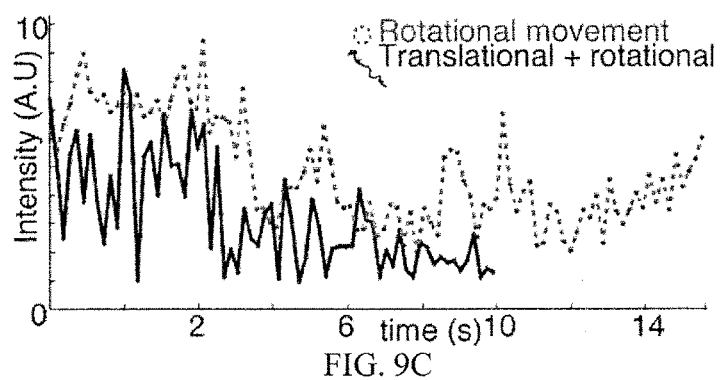
Figure 9B:
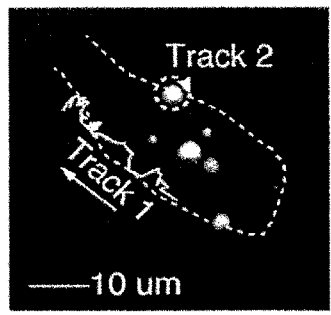
Figure 9D:
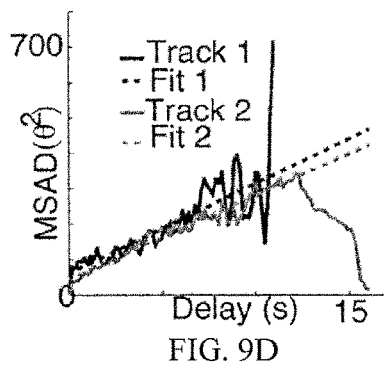
Figure 9E:
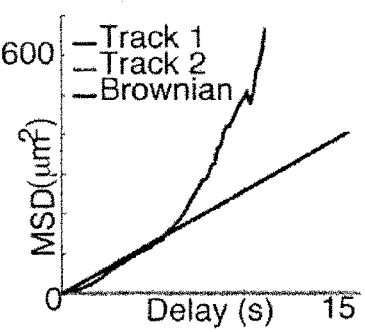

FIGS. 9A-9E demonstrate the possibilities of a time resolved imaging of living cells. 100 nm diameter SHG active $KNbO_3$ particles were injected into human epithelial cells by electroporation. FIG. 9A shows a wide field image, and FIG. 9B shows a time integrated stack of SHG images of the cells that now contain 100 nm particles. The arrows in FIG. 9B indicate the particle motion. It can be seen that one particle (encircled) is restricted by the cell and another particle is being ejected by the cell (arrow). The tracks of both these particles are shown in FIG. 9C. From the position and intensity of the tracks the mean square angular (FIG. 9D) and spatial (FIG. 9E) displacement can be determined The tracking of particle motion with SHG and the interaction of the particle with the electric field of the laser pulses allows for the extraction of both translational and rotational motion Having those numbers the local cell response as well as the micro viscosity can be determined. Currently the state of the art (due to the need for scanning) is ~1 s. Using coated $BaTiO_3$ particles we can take images with only 0.5 milliseconds acquisition time. Such particles can be coated with proteins and antibodies, and because they have a strong SHG signal, which originates from <100 nm, they can be used for super resolution imaging of biological specificity.

Figures 10A, 10B, 10C, 10D:
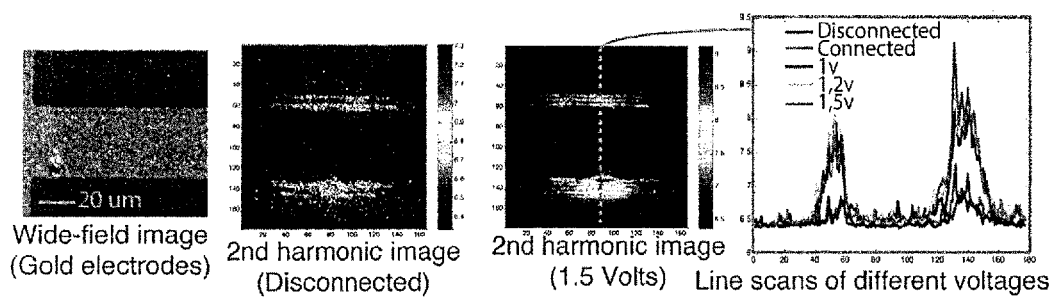
FIGS. 10A-10D shows a wide field image of two gold electrodes (FIG. 10A), a SHG image showing plasmons at the interface (FIG. 10B), a SHG image when a potential of 1.5 V is applied (FIG. 10C), and the intensities (FIG. 10D) measured under different conditions along the dotted line in FIG. 10C.

FIGS. 10A-10D demonstrate the possibility of voltage sensing, and monitoring surface plasmons and electrochemistry. FIG. 10A shows a wide field image of two 50 nm-thick (perpendicular to the image plane) gold electrodes, in water. FIG. 10B shows the SHG image of the electrodes, wherein the plasmons at the interface are visible. FIG. 10C shows the SHG image, when a potential of 1.5 V is applied between the electrodes, and FIG. 10D shows the SHG intensity along the dotted line for disconnected electrodes, connected electrodes, and for potentials of 1.0V, 1.2V, and 1.5 V applied between the electrodes. The application of a voltage is seen to both enhance the SHG signal (due to voltage dependence), and to change the plasmon frequency (material property of the electrodes).

Figures 11A, 11B, 11C:
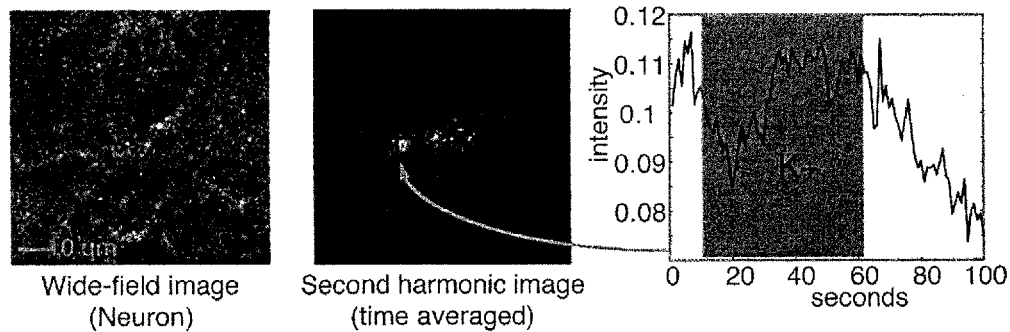
FIGS. 11A-11C show a neuronal junction (synapse) that is stimulated with drugs to change its membrane potential.

FIGS. 11A-11C show a neuronal junction (synapse) that is stimulated with drugs to change its membrane potential. FIG. 11A shows a wide field phase contrast image, FIG. 11B shows a time averaged SHG wide field image, and FIG. 11C shows a time trace of the SHG signal intensity at the point indicated by the arrow. The time trace correlates with an independently measured action potential signal. The data shows the possibility of multisite imaging of neuronal activity comprising electrical, metabolic, and structural changes. The fluence at which these cultured living mouse brain neurons were imaged was 7 mJ/cm$^2$, which is more than two orders of magnitude lower than the current state of the art obtained with SHG imaging in point scanning mode (3400 mJ/cm$^2$) [27].

Various additional modifications may be provided to the above described embodiments without leaving the scope of the invention which is defined by the annexed claims.

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and non-volatile media, transitory and non-transitory, transient and non-transient media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile disks (DVD), holographic media or other optical disk storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] S. Roke and G. Gonella, Ann. Rev. Phys. Chem. 63, 353-378, (2012).
[2] H. Wang, E. C. Y. Yan, E. Borguet, and K. B. Eisenthal, Chem. Phys. Lett. 259, 15 (1996).
[3] J. Shan, J. I. Dadap, I. Stiopkin, G. A. Reider, and T. F. Heinz, Phys. Rev. A 73, 023819 (2006).
[4] N. Yang, W. E. Angerer, and A. G. Yodh, Phys. Rev. Lett. 87, 103902 (2001).
[5] S. H. Jen, G. Gonella, and H. L. Dai, J. Phys. Chem. A. 113, 4758 (2009).

[6] B. Schürer, S. Wunderlich, C. Sauerbeck, U. Peschel, and W. Peukert, Phys. Rev. B 82, 241404 (2010).
[7] U.S. Pat. No. 6,055,051, K. B. Eisenthal, Method for determining surface properties of microparticles, 2000.
[8] Y. Liu, C. Y. Yan, X. L. Zhao, and K. B. Eisenthal, Langmuir 17, 2063 (2001).
[9] *Handbook of Biomedical Nonlinear Optical Microscopy*, edited by B. Masters and P. T. C. So (Oxford University Press, Oxford, 2008).
[10] I. Freund, M. Deutsch, and A. Sprecher, Biophys J. 50, 693 (1986).
[11] M. Nuriya, J. Jiang, B. Nemet, K. B. Eisenthal, and R. Yuste, PNAS 103, 786 (2006).
[12] P. J. Campagnola, M.-D. Wei, A. Lewis, and L. M. Loew, Biophys. J. 77, 3341 (1999).
[13] M. Kriech and J. C. Conboy, J. Am. Chem. Soc. 127, 2834 (2005)
[14] Oron D, Tal E, Silberberg Y., Opt Express. 13(5):1468 (2005).
[15] Peterson M D, Hayes P L, Martinez I S, et al. Opt Mater Express, 1(1):57 (2011).
[16] Nikolenko, Volodymyr et al. Frontiers in Neural Circuits 2:5 (2008).
[17] K. Kuetemeyer, R. Rezgui, H. Lubatschowski, and A. Heisterkamp, Biomed. Opt. Express 1, 593 (2010).
[18] Pantazis, P., Maloney, J., Wu, D., and Fraser, S. E., Proc Natl Acad Sci USA 07(33):14535-40. (2010).
[19] Cho S H, Kärtner F X, Morgner U, et al. Opt Lett. 26(8):560 (2001).
[20] Major A, Cisek R., Neev J, Nolte S, Heisterkamp A, Schaffer C B. Proc SPIE. 6881(2008).
[21] Le Harzic R, Riemann I, Konig K, Williner C, Donitzky C. *J Appl Phys.* 102(11):114701, (2007).
[22] del Barco, O., and Bueno, J. M., J. Biomed. Opt. 17, no. 4 0450051-0450058, (2012).
[23] J. I. Dadap, H. B. de Aguiar, and S. Roke, J. Chem. Phys. 130, 214710 (2009).
[24] L. Haber, S. J. Kwok, M. Semeraro, and K. B. Eisenthal, Chem. Phys. Lett. 507, 11 (2011).
[25] C. Maurer, A. Jesacher, S. Bernet, and M. Ritsch-Marte, Laser Photon. Rev. 5(1), 81-101, WILEY-VCH Verlag (2011).
[26] J. Mertz, Nature methods 8, no. 10: 811-819 (2011).
[27] D. A. Dombeck, K. A. Kasischke, H. D. Vishwasrao, M. Ingelsson, B. T. Hyman, and W. W. Webb, Proc. Natl. Acad. Sci. U.S.A. 100(12), 7081-7086 (2003).

The invention claimed is:

1. A method for detecting or imaging second harmonic generation and multi-photon scattered radiation scattered from a sample including a turbid medium, comprising:
providing a beam of laser pulses from a laser source,
wherein the laser pulses of the beam of laser pulses from the laser source have a pulse energy of more than 10 nJ and a repetition rate of less than 10 MHz;
splitting the beam of laser pulses into two or more partial beams and focusing and overlapping the two or more partial beams on a spot on a sample including a turbid medium; and
detecting or imaging second harmonic generation and multi photon scattered radiation scattered from the spot on the sample.

2. The method of claim 1,
wherein the laser source has a repetition rate of less than 1 MHz and more than 150 kHz.

3. The method of claim 1,
wherein the laser pulses of the beam of laser pulses from the laser source have a pulse energy of more than 50 nJ.

4. The method of claim 1,
wherein the two or more partial beams are focused on the spot on the sample with a focus having a diameter of more than 10 μm.

5. The method of claim 1,
wherein detecting or imaging second harmonic generation and multi-photon scattered radiation scattered from the spot on the sample comprises detecting second harmonic generation and multi-photon scattered radiation scattered from the spot on the sample, and
wherein the second harmonic generation and multi-photon scattered radiation scattered from the spot on the sample is detected using a gated photon counting technique.

6. The method of claim 1,
wherein each partial beam of the two or more partial beams is polarized.

7. The method of claim 6,
wherein each partial beam of the two or more partial beams has a corresponding state of polarization that is different than a corresponding state of polarization of each of the other partial beams of the two or more partial beams, and
wherein a corresponding at least one state of polarization of at least one partial beam of the two or more partial beams is selected from the group consisting of: linear, circular, and elliptical.

8. The method of claim 1, further comprising:
modifying one or more of the following:
an amplitude, a state of polarization, a phase, a delay, and a temporal profile, of laser pulses of at least one partial beam of the two or more partial beams.

9. The method of claim 1,
wherein detecting or imaging second harmonic generation and multi-photon scattered radiation scattered from the spot on the sample comprises imaging second harmonic generation and multi-photon radiation scattered from the spot on the sample, and
wherein an acquisition time for imaging second harmonic generation and multi-photon scattered radiation scattered from the spot on the sample is in the range between 1 μs and 1 s.

10. A system for detecting or imaging second harmonic generation and multi-photon scattered radiation scattered from a sample including a turbid medium, comprising:
a laser source,
wherein the laser source outputs a beam of laser pulses, and
wherein the laser pulses of the beam of laser pulses from the laser source have a pulse energy of more than 50 nJ and a repetition rate of less than 1 MHz;
a beam splitter arranged to receive the beam of laser pulses and to split the beam of laser pulses into two or more partial beams; and
a detector,
wherein the detector is arranged to detect second harmonic generation and multi-photon scattered radiation scattered from a sample on which the two or more partial beams are focused and overlapped.

11. The system of claim 10,
wherein the laser pulses of the beam of laser pulses from the laser source are focused on the sample with a focus having a diameter of at least 10 μm.

12. The system of claim 10, further comprising:
a photon counter coupled to the detector,
wherein the photon counter is adjusted to count photons within predetermined time intervals.

13. The system of claim 10,
wherein a corresponding at least one path length of at least one partial beam of the two or more partial beams is varied with respect to a corresponding path length of each of the other partial beams of the two or more partial beams.

14. The system of claim 10,
wherein the beam splitter is arranged to split the beam of laser pulses into a first partial beam of the two or more partial beams having a first state of polarization and a second partial beam of the two or more partial beams having a second state of polarization, and
wherein the second state of polarization is different than the first state of polarization.

15. The system of claim 10,
wherein a corresponding at least one state of polarization of at least one partial beam of the two or more partial beams is controllably varied to be one of the following: linear, elliptical, and circular.

16. The system of claim 10, further comprising:
the sample,
wherein the sample includes one or more of the following: a turbid medium, a particle, a bubble, a droplet, a virus, a micelle, a liposome, and a living cell.

17. The system of claim 10,
wherein the beam splitter comprises a reciprocal phase-polarization-time control unit, and
wherein the reciprocal phase-polarization-time control unit comprises:
    a first telescopic system to decrease a beam diameter of the received beam of laser pulses;
    a beam displacer to split the received beam of laser pulses into two collinear beams having orthogonal polarizations relative to each other;
    a second telescopic system to increase a corresponding two beam diameters of, and spatially separate, the two collinear beams;
    a cubic mirror;
    a time delay stage; and
    a spatial light modulator operable in reflection mode.

18. The system of claim 10, further comprising:
a spatial light modulator,
wherein the spatial light modulator is configured to modify one or more of the following:
    an amplitude, a polarization, a phase, a delay of pulses, and a temporal profile, of laser pulses of at least one partial beam of the two or more partial beams.

19. The system of claim 10,
wherein the system is a static wide field scattered harmonic generation and multi-photon microscope,
wherein the system further comprises an imaging objective lens that receives the second harmonic generation and multi-photon scattered radiation scattered from the sample,
wherein the two or more partial beams are two partial beams,
wherein the two partial beams are weakly focused and then simultaneously illuminate a large portion of the sample at an angle,
wherein the angle is such that two partial beams do not damage the imaging objective lens of the detector, and
wherein the angle is such as to allow an analysis of eight possible polarization combinations that can be used to perform orientational analysis.

20. The system of claim 10,
wherein the system is a static wide field scattered harmonic generation and multi-photon microscope,
wherein the two or more partial beams are two or more composite partial beams,
wherein the system further comprises:
    two high NA lenses between which the sample is positioned,
wherein the two or more composite partial beams enter each of the two high NA lenses off-centered and the two or more composite partial beams exit each of the two high NA lenses at an angle and overlap at a corresponding focal plane of the corresponding high NA lens of the two high NA lenses, and
wherein the sample is placed at the focal plane of both of the two high NA lenses.

21. A non-transitory computer readable medium containing a set of instructions that when executed cause a computer to perform a method of producing an image or spectra, wherein the method of producing an image or spectra comprises:
    receiving data resulting from a method for detecting or imaging second harmonic generation and multi-photon scattered radiation scattered from a sample including a turbid medium,
    wherein the method for detecting or imaging second harmonic generation and multi-photon scattered radiation scattered from a sample including a turbid medium comprises:
        providing a beam of laser pulses from a laser source,
        wherein the laser pulses of the beam of laser pulses from the laser source have a pulse energy of more than 10 nJ and a repetition rate of less than 10 MHz;
        splitting the beam of laser pulses into two or more partial beams and focusing and overlapping the two or more partial beams on a spot on a sample including a turbid medium; and
        detecting or imaging second harmonic generation and multi photon scattered radiation scattered from the spot on the sample;
    processing the data; and
    producing an image or spectra corresponding to the data.

* * * * *